(12) United States Patent
Caskey

(10) Patent No.: US 7,714,183 B2
(45) Date of Patent: May 11, 2010

(54) USE OF HONEY IN DRESSINGS

(75) Inventor: Phillip Roy Caskey, Cambridge (NZ)

(73) Assignee: Apimed Medical Honey Limited, Cambridge (NZ)

( * ) Notice: Subject to any disclaimer, the term of this patent is extended or adjusted under 35 U.S.C. 154(b) by 410 days.

(21) Appl. No.: 10/312,742

(22) PCT Filed: Jun. 29, 2001

(86) PCT No.: PCT/NZ01/00129

§ 371 (c)(1), (2), (4) Date: Sep. 16, 2003

(87) PCT Pub. No.: WO02/00269

PCT Pub. Date: Jan. 3, 2002

(65) Prior Publication Data

US 2004/0127826 A1    Jul. 1, 2004

(30) Foreign Application Priority Data

Jun. 30, 2000   (NZ) .................................. 505514

(51) Int. Cl.
*A61F 13/00* (2006.01)

(52) U.S. Cl. .................. 602/48; 602/41; 602/42; 604/304

(58) Field of Classification Search ........... 602/41–59; 604/304–308; 424/443–449, 402, 404; 128/888, 128/889

See application file for complete search history.

(56) References Cited

U.S. PATENT DOCUMENTS

| | | | | |
|---|---|---|---|---|
| 2,432,541 | A | * | 12/1947 | McClelland .................. 602/48 |
| 4,562,110 | A | * | 12/1985 | Tong ........................... 442/368 |
| 5,197,945 | A | * | 3/1993 | Cole et al. .................... 602/49 |
| 5,407,675 | A | | 4/1995 | Etemad-Moghadam |
| 5,456,745 | A | | 10/1995 | Harold et al. |
| 5,980,875 | A | | 11/1999 | Mousa |
| 6,319,510 | B1 | | 11/2001 | Yates |

FOREIGN PATENT DOCUMENTS

| | | |
|---|---|---|
| EP | 0 353 896 | 2/1990 |
| EP | 0 355 536 A2 | 2/1990 |
| WO | WO 00 09176 | 2/2000 |
| WO | WO 01 41776 | 6/2001 |
| WO | WO 01 67888 | 9/2001 |
| WO | WO 02087644 A1 * | 11/2002 |

OTHER PUBLICATIONS

Molan, Charles, Wold Wide Wounds, Honey as a topical antibacterial agent for treatment of infected wounds, Dec. 2001, pp. 1-33.*
Subrahmanyam, M. Honey Impregnated Gauze Versus Polyurethane Film (OpSite) in the Treatment of Burns—A prospective randomized Study, Br J. Plast Surg. Jun. 1993; 46(4) pp. 322-323.*
U.S. Appl. No. 60/130,341, filed Apr. 20, 1999.*
Molan P.C. et al. "The Effect of Gamma-Irradiation On The Antibacterial Activity of Honey." *Journal of Pharmacy and Pharmacology.* London, vol. 48, No. 11. Nov. 1996, pp. 1206-1209.
Allen K.L. et al. "A Survey of the Antibacterial Activity of Some New Zealand Honeys," *Journal of Pharmacy and Pharmacology,* London, vol. 43, No. 12, Dec. 1991, pp. 817-822.

* cited by examiner

*Primary Examiner*—Kim M Lewis
(74) *Attorney, Agent, or Firm*—Sughrue Mion, PLLC

(57) ABSTRACT

A flexible dressing for direct application to a wound for absorbing exudates. The dressing comprises an alginate fiber sheet having honey fully impregnated through the fiber sheet such that the dressing has moist surfaces, and on application to the wound, the dressing becomes gel-like as exudate is absorbed.

11 Claims, 2 Drawing Sheets

USE OF HONEY IN DRESSINGS

TECHNICAL FIELD

This invention is directed to improvements in and relating to the use of honey in dressings. In particular, it is envisaged honey, having preferred qualities and viscosity, will be used in conjunction with a range of therapeutic and/or appropriate medical dressings and will be used as a healing barrier for wounds.

Honey impregnated dressings accordingly will find application in chronic wound care for both non-infected and infected wounds, particularly where moist wound care is desired.

However, it should be appreciated that aspects of this invention may have applications outside this field.

BACKGROUND ART

The need for alternatives in chronic wound care has been identified. Products available in the chronic wound care market have been developed to shorten the "episode of care" associated with managing hard-to-heal wounds. An increased awareness of moist wound healing, particularly the chronic wound care has also developed significantly over the last few years in both the public and private healthcare sectors.

Chronic wounds are identified as wounds that are unable to heal by primary intervention, and are assessed on three major indices:
a) exudate level,
b) tissue types present; and
c) depth of wound.

Other important factors include the presence of infection, underlying disease aetiology, the patient's general condition, and co-existing disease or medications.

In relation to chronic wound care, two main categories of wounds can be recognised with which appropriate wound care products as described by the present application would be applied. These two main categories are:
a) exudating wounds that are not infected; and
b) exudating wounds that are infected.

The majority of chronic wounds fall within the first category. These wounds may be managed by moist wound healing principles, although the healing process is not complicated by infection.

The second category includes chronic wounds that will not heal until complete eradication of the infection has first been achieved. Accordingly, within this category of wounds, wound healing is not the primary aim. However, once the infection is under control, non-active healing products are generally used.

This second category of wounds is among the hardest sector to treat, whilst there is a wide range of products used both topically and systemically for clearing wound infections, (including iodine-based preparations and so forth), the main therapeutic intervention for infective wounds however, is the use of systemic antibiotics.

However, existing antibacterial treatments may have varying effectiveness, and some have been shown to cause tissue damage and slowing down of the healing process. Honey on the other hand, appears to actually promote the healing process with no corresponding tissue damage. Historically, honey has been identified as having healing properties. Recently however, anti-microbial properties of certain honey and their potential use in wound care have attracted attention.

In New Zealand, the "unique Manuka factor" (UMF™) activity identified in Manuka tree-based honey products, and in other active honey products produced from the plant species *Leptospermum*, has been identified to be useful in relation to infected wounds. Although, ordinary honey may nevertheless also have application for non-infected wounds.

The beneficial properties of some particular honeys, (particularly Manuka honey) include both its anti-bacterial, non-peroxide activity, as well as its peroxide activity. The non-peroxide anti-bacterial activity of these honeys has been shown to inhibit the growth of various species of bacteria and limit the production of the undesirable bi-products of bacterial growth. Honey with at least 10% non-peroxide activity (10% phenol equivalent) demonstrates such therapeutic value.

Whilst the application of honey to wounds is known within the prior art, the use of honey in relation to dressings applied to wounds is still developing.

However, it is important when a dressing is applied to a wound that the dressing itself does not stick to the wound. When the dressing is removed, any healing that may have begun, in terms of skin replacement and so forth may be undone where the surface of the skin sticks to the dressing and is removed when the dressing is removed. As can be appreciated this delays the healing process and recovery overall.

However, healing processes will not usually occur unless infection is cleared from the wound.

Honey based products, particularly UMF™ honey, play a role in managing infected wounds when applied or used in conjunction with appropriate dressings. Honey based wound dressings inherently have a number of properties that lend them to use as general chronic wound care dressings in particular. These properties include:
a) osmotic absorption of excess exudate; and
b) inherent peroxide (antibacterial) activities; which is both wound cleansing and helps with wound bed oxygenation; and
c) provision of beneficial nutrients to the wound bed.

Whilst honey can be applied to an area, the usual fluidity of honey has made localised application difficult. Even the use of absorbent material (such as existing bandages or gauzes), have not successfully addressed inherent difficulties relating to the application of honey to, and its maintenance on, the wound area. Given exudating wounds exacerbate this problem the need is identified to produce an appropriate dressing in conjunction with honey in a form that overcomes the above problems.

In addition, to facilitate wound healing it is preferable that the honey be of a preferred viscosity (whether achieved via specific processing of the honey or not) and/or include concentrated beneficial properties.

It would also be beneficial to make maximum use of the hygroscopic characteristic of honey—(capable of absorbing moisture from the air) that provides an advantage to using honey in moist wound care.

Therefore, it would be advantageous to develop the use of honey-based wound dressings that may be used:
a) in relation to the care of chronic wounds, including non-infected as well as infected wounds; and
b) to meet the requirements of moist wound care practices; and
c) to promote the healing barrier, as opposed to the use of dressings which when removed may delay overall healing; and
d) including honey-based products containing higher proportions of active and/or honey with preferred properties; and
e) in the care not only of wounds, but also burns and skin ulcers for more rapid healing, with minimal scarring.

Modern hydro-colloid wound dressings are presently favoured as moist dressings, although such wound dressings are expensive. Foams, gels and alginates are also available for treating chronic wounds. However, whilst moist wound care enhances the healing process through tissue re-growth, such moist conditions favour the growth of infecting bacteria.

The use of honey in conjunction with dressings has shown however that infecting bacteria are disadvantaged.

It is an object of the present invention to at least provide a wound dressing with which honey is used that addresses the above-mentioned problems, and/or provide the public with a useful choice.

Further aspects and advantages of the present invention will become apparent from the ensuing description which is given by way of example only.

DISCLOSURE OF INVENTION

According to one aspect of the present invention there is provided a method of manufacturing a dressing for use as a moist application, said method including the steps of:

a) preparing a composition including at least one honey in a preferred form; and
b) combining said honey composition with a preferred base material;

characterised in that the honey composition effects a change in the physical characteristics of the dressing.

According to another aspect of the present invention there is provided a method of manufacturing a dressing substantially as described above wherein the base material is configured in the form of a film, a strip or a patch dressing, or a rope dressing.

According to another aspect of the present invention there is provided a method of manufacturing a dressing substantially as described above wherein the base material is configured in a form selected from a single substantially uniform layer; multiple layers; a "rope" form; and a woven, moulded form. Optionally, one or more types of base materials are used, including material which encase another material.

According to another aspect of the present invention there is provided a method of manufacturing a dressing substantially as described above wherein said dressing is applied substantially moist in use on or in relation to either or both infected and non-infected chronic wounds.

According to another aspect of the present invention there is provided a method of manufacturing a dressing substantially as described above wherein the base material includes at least one or more of the group; a substantially waterproof backing layer; an adhesive portion; and a retention dressing.

According to another aspect of the present invention there is provided a method of manufacturing a dressing substantially as described above wherein the required consistency of the finished honey composition will dictate the quantities of the forms of honey used.

According to another aspect of the present invention there is provided a method of manufacturing a dressing substantially as described above, wherein the base material includes an agent selected from: a moisture absorbing agent; a moisture trapping agent; a moisture removing agent; and a combination thereof.

According to another aspect of the present invention there is provided a method of manufacturing a dressing substantially as described above, wherein the honey composition includes an agent selected from: a moisture absorbing agent; a moisture trapping agent; a moisture removing agent; and a combination thereof.

According to another aspect of the present invention there is provided a method of manufacturing a dressing substantially as described above in which the dressing is substantially flexible.

According to another aspect of the present invention there is provided a method of manufacturing a dressing substantially as described above in which the honey composition applied to the base material varyingly impregnates said base material, from a surface application on one side of said base material to a fully impregnated base material.

According to another aspect of the present invention there is provided a method of manufacturing a dressing substantially as described above wherein the honey composition may have a variable viscosity depending on the base material with which it is used.

According to another aspect of the present invention there is provided a method of manufacturing a dressing substantially as described above wherein the honey composition includes honey in substantially concentrated form.

According to another aspect of the present invention there is provided a method of manufacturing a dressing substantially as described above wherein the base material is selected from: an alginate; a hydro-colloid; a foam; a gel material; and a combination thereof.

According to another aspect of the present invention there is provided a method of manufacturing a dressing substantially as described above wherein the base material further includes at least one compound selected from: a pharmaceutical; a vitamin; a hormone; a chemical compound; a chemical element; a cation; a plant extract; a gelling agent (whether synthetic or otherwise); and a combination thereof.

According to another aspect of the present invention there is provided a method of manufacturing a dressing substantially as described above wherein said base material(s) are substantially sterile.

According to another aspect of the present invention there is provided a method of manufacturing a dressing substantially as described above wherein the honey composition includes a combination of one or more honeys including active honey, being a honey having higher than 10% non-peroxide activity, and/or non-active honey.

According to another aspect of the present invention there is provided a method of manufacturing a dressing substantially as described above wherein the honey composition is selected from dried honey; creamed honey; crystallised honey; liquid honey; and a combination thereof.

According to another aspect of the present invention there is provided a method of manufacturing a dressing substantially as described above wherein the dried honey is selected form spray dried honey; freeze dried honey; oven dried honey; air dried honey; and a combination thereof.

According to another aspect of the present invention there is provided a method of manufacturing a dressing substantially as described above wherein the required consistency of the finished honey composition will dictate the quantities of the forms of honey used.

According to another aspect of the present invention there is provided a method of manufacturing a dressing substantially as described above, wherein the dressing includes moisture absorbing, trapping, or removing agent suitable for removing exudate from a wound for an extended period of time after application to a wound.

According to another aspect of the present invention there is provided a method of manufacturing a dressing substantially as described above in which the dressing is substantially flexible.

According to another aspect of the present invention there is provided a method of manufacturing a dressing substantially as described above wherein the dressing provides and/or promotes at least one of:
a) a moist environment;
b) a non-stick barrier;
c) healing properties to speed up healing and minimise scarring;
d) an anti-microbial environment;
e) an exudate absorbing environment;
f) reduced requirement for anaesthetics;
g) an anti-inflammatory action; and
h) deodorising action, providing an odour free or odour reduced environment;
i) epithelialisation;
j) cleansing; and
k) debriding action.

According to another aspect of the present invention there is provided a dressing manufactured in accordance with the method substantially as described above.

According to another aspect of the present invention there is provided a dressing substantially as described above wherein the base material may include and/or be used in conjunction with at least one or more substantially waterproof backing layer, an adhesive portion, a retention dressing.

According to a further aspect of the present invention there is provided a dressing substantially as described above, comprising at least a honey composition and a base material, sterilised by irradiation.

According to another aspect of the present invention there is provided a honey composition for use in either or both the method and the dressing substantially as described above.

In preferred embodiments of the present invention, the honey composition includes a substantial proportion of, or a substantially concentrated form of honey to provide optimum availability of the beneficial properties of the honey with the dressing. The honey composition preferably includes an active honey, being a honey having higher than phenol equivalent, particularly where the dressing is used in relation to sites infected by bacteria and so forth. However, non-active honey may also be used alone, or in combination with active honey.

In New Zealand, honey such as that derived from plants of the genus *Leptospermum* (particularly Manuka, Rewa Rewa and so forth) demonstrate unique non-peroxide activity (anti-microbial activity), as well as peroxide activity (oxygenating and/or cleansing activity). The non-peroxide activity of honey has been found to be advantageous or even therapeutic with respect to moist wound care of infected wounds.

Preferably, such active honey requires a 10% phenol equivalent to be of optimum therapeutic value. In New Zealand Manuka honey has reliably demonstrated such activity, although a range of other honeys may also demonstrate active properties to a greater or lesser extent and may also be used with this invention.

A number of honeys do not demonstrate such active properties, but may nevertheless be used alone or in conjunction with active honey to produce the honey-based composition of the present invention, particularly for use with dressings for non-infected moist wound care purposes.

In order to preserve or maintain any of the active properties of the honey used in the honey composition, it is preferable that temperatures involved in the manufacturing of the honey composition be maintained at low-levels (or at high temperatures for a very short period(s) of time). Prolonged exposure to high temperatures destroys the active properties of active honey.

The honey composition of the present invention may be produced using honey in a variety of forms, either alone or in combination. Such forms preferably include dried powdered form (spray dried, air dried, low temperature, oven dried or freeze dried) liquid form, creamed form or crystallised form.

As can be appreciated, the quantities of the various forms of honey will vary depending on the required consistency and concentrated properties of the finished product. For example, use of spray dried honey in the composition will increase the viscosity and concentrate the active and non-active honey properties. The various combinations of dried honey to non-dried honey will also influence the malleability of the honey product.

The honey composition of preferred embodiments may also include other agents. Said other agents including a gelling agent, pharmaceuticals, (an antibiotic), vitamins (such as Vitamin A), cations (such as calcium to assist blood clotting), plant extracts (to facilitate wound healing), and so forth as required to produce a honey composition having the required consistency and properties for appropriate chronic wound care.

Given the hygroscopic nature of honey, controlling the relative humidity during preparation of the honey-composition preferably improves both the handling of the honey mixture and the product produced.

Once the preferred honey-based composition is produced, the composition may be applied to an appropriate base material for subsequent application as a dressing for chronic wound care.

In some preferred embodiments of the present invention, the base material may be a gel. For example, a gel may be prepared by dissolving a gelling agent, such as agar, in an agar solvent (such as water). The gel is allowed to solidify in a suitable form such as a film. The gel is then preferably soaked in the preferred honey composition to allow some or all of the agar solvent to be replaced by honey through a process of diffusion.

Accordingly, the product so produced is in the form of a soft adherent gel that may be applied as a dressing to an infected or non-infected wound depending upon whether the honey composition was prepared from honey including active or "non-active" honey. This form of the dressing may be most suitable for use in burn care applications. The honey provides the healing barrier, the agar provides a physical barrier. As the burn heals the agar honey dressing may be washed away.

In other preferred embodiments the alternative preferred base material is an alginate dressing. Such alginate dressings are available in the prior art as either strips, patches or in rope form as packing.

The properties of the alginate dressings are such that a substantially less viscous honey composition may be applied to the alginate dressing and be absorbed thereby to varying degrees. For example, the alginate dressing effectively operates as a sponge and soaks up the honey into the alginate dressing. The quantity of honey used in relation to the dressing will dictate whether the honey is fully absorbed throughout the alginate dressing or penetrates only a limited distance within thickness of the alginate dressing.

The varying characteristics of the alginate dressing in conjunction with the hygroscopic nature and fluid nature of the honey results in the overall wound dressing becoming gel-like with substantially moist surface(s). Accordingly, the honey composition-base material wound dressing may then be applied as a moist wound dressing to either or both infected and non-infected wounds dependent upon the honey used in the composition. They gel-like nature of the dressing and the substantially moist interface between the dressing and the wound reduces the likelihood of the dressing sticking to the wound and thereby improves the healing process.

The gel-like consistency of the dressing also improves the malleability of the dressing to effect optimum contact with the site. This form of dressing has also demonstrated advantageous absorption of wound exudate.

In preferred embodiments, the honey composition-base material dressing is such that it may be moulded or plied into shape by finger pressure, or may simply be draped across and conform to the shape of the area covered by the dressing.

Preferably, the wound dressing and particularly the honey-composition is required to be in intimate contact with the surface of the wound in order to effect preferred healing.

The honey interface between the wound and the dressing maintains the area moist for improved healing to occur. Where active honey is used healing of infected wounds is promoted. The dressings can also be retained on the wound for extended periods of time and even absorb exudate from the wound depending on the wound. Some applications may require replacement of the dressing at least once a day. The base material preferably localising the extra moisture in the specific area. In addition, the moist dressing may be removed freely without risk of removal of "scabbing" or new skin formed over the wound, and without the pain that may accompany removal of traditional dressings.

Typically, the wound dressing is applied to the area required and maintained in place either by virtue of the surface tension created between the body and the moist wound dressing (particularly where the patient is lying down), or may be held in place by appropriate additional dressings such as bandages, adhesive strips integral with or used in conjunction with the dressing, and so forth.

Given the hygroscopic nature of honey, it may be necessary to increase the viscosity of the honey by the addition of a gelling agent to minimise the effects of body and room temperature as well as moisture in the air on the fluid content of the dressing.

Where additional agents and so forth are added to or included in the honey composition, such factors regarding the suitability for medical or intended use, stability over time, compatibility with honey and the ability to form the composition having the desired physical and therapeutic properties must be considered. Such factors will of course be dictated by the requirements of use or the intended purpose.

A number of gelling agents are available in the prior art, including various scums, polysaccharides, alginates and so forth. Given the known gelling properties of alginate makes the application of the honey composition to an alginate dressing particularly relevant for the present invention. However, alginate is only one form of a base material that may be used. Base materials produced from or including other gelling agents may also have application with the present invention. Hydro-colloids and foams may also be used with varying success. However, hydro-colloids and hydrogels whilst useful, tend to absorb less fluids than the alginates and therefore may not be appropriate for use with heavily exudating wounds, where alginates are found to perform better.

Other optional agents added to or used in conjunction with the dressing include cations, such as calcium. These may be added to the honey composition and/or to the base material. For example, calcium alginate dressings are particularly useful where there is bleeding, as calcium can promote blood clotting. Other agents impregnated into the alginate dressings may also have varying uses depending on the application required.

Various actives/agents may also be included to address particular concerns that extend beyond the ability of the honey, or which are provided as supplements to the performance of the honey or augment the performance of the honey. These may include fungicides, antibiotics, vitamins, plant extracts (including flavanoids, aromatic acids, anti-inflammatory compounds) and so forth.

In preferred embodiments the honey composition-base material wound dressing is irradiated to produce a sterile wound dressing.

Given the particular properties of the dressing, it is typically envisaged that a suitable backing sheet, preferably waterproof (such as plastic or a similar type of sheet material) surround the wound dressing or packaging surfaces to maintain the moistness of the dressing as well as preserving the other beneficial properties of the dressing.

As can be appreciated, variations can be made in relation to the overall honey composition as described above whether it is in relation to the form of the honey used in the composition, the viscosity of the honey, the concentration, or the inclusion of an optional components.

It also can be appreciated, that variations can be made to the base material with which the honey composition is used depending on the preferred qualities of the dressing, such as the base material's absorptive properties and the physical structure of, or chemical properties associated with, the base material that would effect a preferred use in relation to the moist care application to a particular wound whether that wound be infected or not.

Wounds with which the dressing may be used include infected and non-infected abrasions, cuts, burns, ulcers, abscesses and so forth.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

The discussion given below as to the method of manufacturing and application of the honey-based wound dressing of the present invention is provided by way of example only, and it should be appreciated that variations to the ingredients of the honey composition, the base material, and the methods of applying or impregnating the base material with the honey composition may be made and included within the scope of the present invention.

With reference to the diagrams by way of example only, there is provided a honey composition-base material wound dressing (generally indicated by arrow 1).

The base material or dressing (2) may include existing/off-the shelf dressings or may be specifically manufactured as layered dressings, agar-gel dressings, woven dressings and so forth, as illustrated in FIGS. 1 to 5 respectively. Rope dressings (not shown) may also be used.

The base material or dressing (2) will vary in thickness depending on the material from which the dressing is made.

Figure 1:
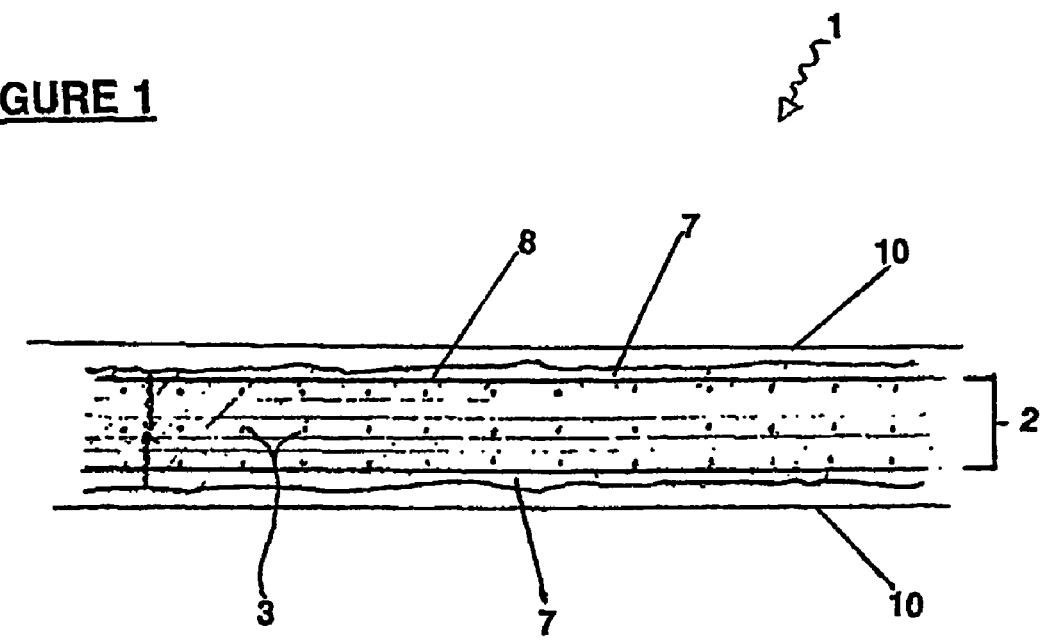
FIG. 1 is a diagrammatic side view of the honey composition-wound dressing in accordance with one possible embodiment of the present invention.

The dressing may include or be impregnated with additional agents/compounds (3) such as calcium to assist in blood clotting (as illustrated in FIG. 1).

Figure 4:
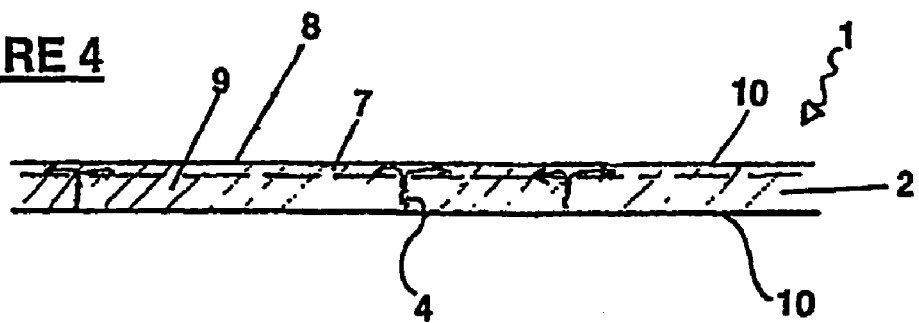
FIG. 4 is a diagrammatic side view of the honey composition-wound dressing in accordance with another possible embodiment of the present invention.
Figure 5:
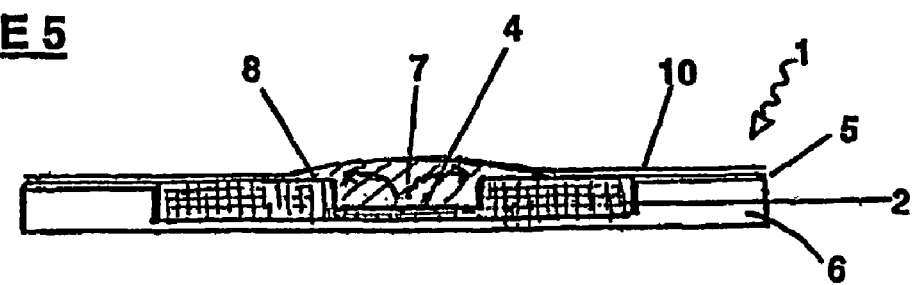
FIG. 5 is a diagrammatic side view of the honey composition-wound dressing in accordance with another possible embodiment of the present invention.

In some embodiments, the dressing (2) may include a reservoir portion (4) into which the honey composition (7) may be applied, as shown in FIGS. 4 and 5, and from which the honey composition (7) is released in use.

The dressing (2) may include adhesive portions (5) to assist in maintaining the dressing in place on or in the vicinity of the wound to which it is applied (as shown in FIG. 5). Although other embodiments of the dressing (2) may require additional dressings (6) such as bandages (6) to maintain the wound dressing (2) in place (shown in FIG. 3).

Figure 2:
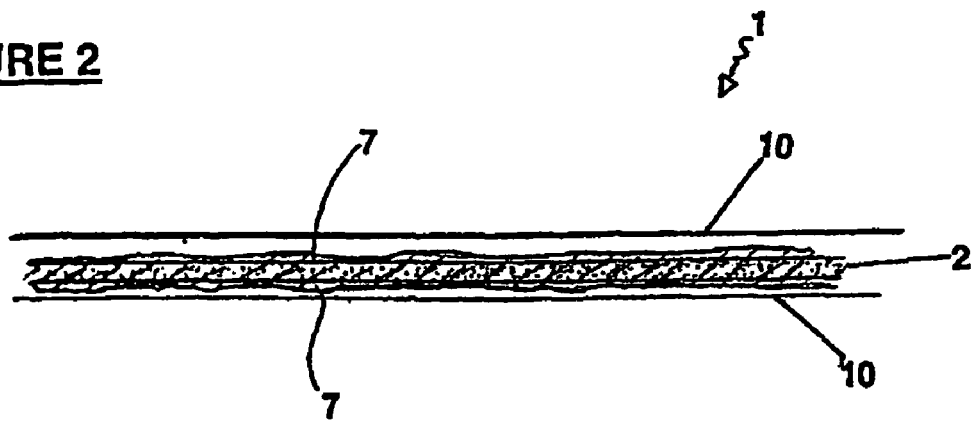
FIG. 2 is a diagrammatic side view of the honey composition-wound dressing in accordance with another possible embodiment of the present invention.
Figure 3:
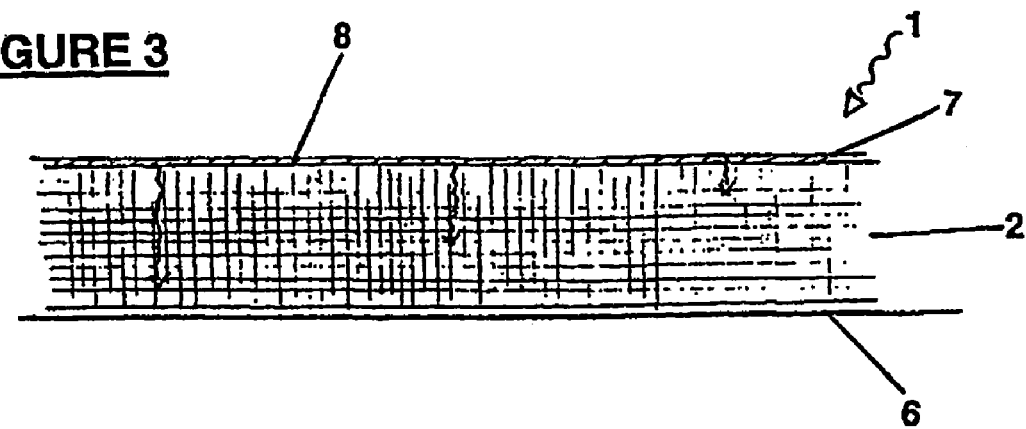
FIG. 3 is a diagrammatic side view of the honey composition-wound dressing in accordance with another possible embodiment of the present invention.

The honey composition (7) may:
a) fully impregnate and/or coat all surfaces of the dressing (2), as shown in FIGS. 1, 2 and 4;
b) be applied to a contact surface (8) of the dressing (2) applied against the wound, as shown in FIG. 3. During use of the wound, exudate may be absorbed into the dressing (2) whilst the honey composition maintains a moist barrier;
c) be retained in reservoirs (4) in the dressing (2), such that the dressing is applied to the wound, the honey composition immediately contacts the wound, or is gradually released onto the wound through aperture (9) in the dressing (as shown in FIGS. 4 and 5, respectively).

Waxed or similar fluid backing material (10) may be applied as one of more surfaces of the wound dressing (2) to maintain the moist property of the dressing prior to use.

EXAMPLE 1

1. Preferred Materials
   Preferred quantity of honey by weight required to be applied or impregnate base material to produce a preferred wound dressing. The honey may include varying percentages by weight of creamed or crystallised honey, spray dried, freeze dried, air dried honey and/or liquid honey.
   Honey used in relation to the wound dressing may be either or both active honey having preferred non-peroxide, antibacterial/antimicrobial properties, and non-active honey not exhibiting non-peroxide activity.
   Optional ingredients including pharmaceuticals (antibiotics, fungicides, other antibacterial agents), vitamin extracts (Vitamin A and so forth), gelling agents, chemical compounds (calcium to promote blood clotting and so forth).
   Base material in the form of a film, woven dressing, layered sheet dressing, patch, strap, rope configuration or wrap. Options for the base material include agar gel film, alginate dressing, hydro-colloid, foam dressing, and so forth.

2. Variations
   The honey may be applied to a dressing in a substantially dried form, particularly for use with exudating wounds. Moisture applied to the wound from an external source, as well as moisture from the exudate may promote the hygroscopic properties of honey to minimise problems associated with too much moisture being in the vicinity of the wound and preventing retention of the dressing on the wound.
   Moisture applied via an external source or via exudate from the wound may facilitate the moist honey barrier between the wound and the dressing, and may even facilitate impregnation of the base material to varying degrees by the honey composition.
   Where the honey based wound dressing is particularly moist such the honey composition is completely absorbed through the base material and presents a substantially moist layer on all surfaces of the dressing, the wound dressing may be retained in place on the wound by use of an additional strip dressing, such as a bandage, plastic wrap, sleeve and so forth.
   Dressings may be varyingly configured for use in particular portions of the body during treatment of particular wounds.
   The extent to which the honey composition impregnates/is absorbed within and forms a surface around the base material will influence the malleability of the wound dressing.
   The thickness of the wound dressing will also impact on the extent to which the wound dressing may conform to the contours of the wound surface.

EXAMPLE 2

Preferred Manufacturing Process
1. The quantities of preferred honey (creamed, crystallised, freeze dried, liquid, spray dried and so forth), are manually mixed together to the required consistency.
   Depending upon whether or not the honey composition is to be used in relation to infected or non-infected wounds, the proportion of active to "non-active" is determined. A high active honey concentration will be required for the treatment of infected wounds.
   Mixing is undertaken preferably at a temperature and relative humidity required to obtain the honey composition having the preferred viscosity.
   The use of high temperatures in relation to the mixing of the honey should be avoided particularly where the composition includes active honey, as high temperatures for prolonged period may destroy the active properties. Where a particularly viscous composition is required, lower temperatures and relative humidity's under 75% are preferred.
2. As required, additional compounds may be added to the mixture during the mixing process. Such compounds may include pharmaceuticals, vitamins, salts and other chemical compounds as required to facilitate the preferred operation of the wound dressing.
3. The preferred base material for receiving the honey may be purchased as an existing product from the prior art (such as existing alginate, hydro-colloid, foam wound dressings—with or without additional components such as calcium and so forth), or may be manufactured as required (such as agar gel films). Depending upon the wound to be treated, the dressing will have a preferred configuration whether as sheet material comprising one or more layers, or otherwise configured (for example in rope form).
4. The honey composition may be applied to the base material by any appropriate means, including but not limited to spray application, pouring or spreading the honey composition onto the base material, or immersing the base material into a substantially fluid quantity of the honey composition and allowing the honey composition to be absorbed therethrough.
5. The base material may be shaped either or both before and after the application of the honey composition to the dressing, depending upon the extent to which the honey composition covers or is absorbed into the base material. Shaping of the base material will be dictated by the ease with which the honey composition-base method wound dressing can be handled at that particular point in the process.
6. The honey composition-base material wound dressing may then be covered by appropriate backing sheet(s) to facilitate packaging of the dressing, and to maintain the preferred moisture content of the dressing.
7. The wound dressing may be appropriately packaged as individual dressings, or as a series of multiple dressing in the one container/receptacle.
8. The wound dressing may be sealed in an air tight package where at least one surface of the package may be waxed or otherwise moisture proof.
9. The wound dressing is preferably irradiated to ensure it is sterile. Any form of appropriate irradiation (such as gama irradiation may be used).

EXAMPLE 3

Application of the Wound Dressing to a Wound
1. The wound to which the dressing is to be applied is identified and may or may not be "cleaned" before the dressing is applied. Where the wound is infected, preferably the honey composition-base material wound dressing will comprise a high proportion of active honey alone or in conjunction with other pharmaceuticals, agents, compounds.
   Where the wound is not infected, the honey composition-wound dressing may comprise a high proportion of non-active honey composition alone, may comprise either or both non-active and active honey composition, alone, or in conjunction with other compounds, agents and so forth.
2. Where the wound is exudating, use of moist wound healing principles may be applied using a wound dressing of the present application that comprises a base material fully impregnated with honey composition providing moisture on all surfaces.
   Where the wounds are not exudating, less moist wound dressings may be applied. For example, honey impregnated, agar-gel dressing may be more appropriate in this instance, and/or may have particular application on burns.
3. The honey composition-base material wound dressing may be self applicating to the surface, or may be maintained in position on the wound by additional dressing material, such as bandages and/or adhesive strips.

Aspects of the present invention have been described by way of example only and it should be appreciated that modifications and additions may be made thereto without departing from the scope thereof.

The invention claimed is:

1. A flexible dressing for direct application to a wound and absorbing exudates comprising:
   (a) honey, and
   (b) an alginate based fibre sheet
   wherein the honey is fully impregnated through the fibre sheet such that the dressing has moist surfaces and on application to a wound, the dressing becomes gel-like as exudate is absorbed.

2. A flexible dressing as claimed in claim 1 wherein the dressing can be moulded to fit the shape of a wound or part of a body to which the dressing in use is applied.

3. A flexible dressing as claimed in claim 1 wherein the wound is moist.

4. A flexible dressing as claimed in claim 1 wherein the wound releases exudate.

5. A flexible dressing as claimed in claim 1 wherein the wound is selected from the group comprising: an ulcer, damaged tissue, a burn, a lesion, an abrasion, a cut, an abscess.

6. A flexible dressing as claimed in claim 1 wherein the honey has peroxide and non-peroxide activity.

7. A flexible dressing as claimed in claim 1 wherein the honey is in a form selected from the group comprising: creamed, crystallised, liquid, dried and reconstituted.

8. A flexible dressing as claimed in claim 1, wherein the fibre is manufactured from [at least one of sodium alginate and] calcium alginate.

9. A flexible dressing as claimed in claim 1 wherein the fibre is in a shape selected from the group comprising: a four-side gauze strip or patch, a rope form, a shape specific to the shape of a wound, a shape specific to a region of the body to which the dressing is applied.

10. A flexible dressing as claimed in claim 1 wherein the honey is fully absorbed and at least partially retained with the fibre.

11. A flexible dressing as claimed in claim 1 wherein the dressing includes a backing layer to retain the dressing in direct contact with the wound when used.

* * * * *